United States Patent [19]

Voss

[11] Patent Number: 5,404,949

[45] Date of Patent: Apr. 11, 1995

[54] LIQUID SAMPLING APPARATUS

[76] Inventor: Gene A. Voss, 4227 Centergate, San Antonio, Tex. 78217

[21] Appl. No.: 241,153

[22] Filed: May 10, 1994

[51] Int. Cl.⁶ ............................................. E21B 49/00
[52] U.S. Cl. .................................................... 166/264
[58] Field of Search ................ 166/264, 162, 165–169; 175/59; 73/864.51, 864.63

[56] References Cited

U.S. PATENT DOCUMENTS

| | | | |
|---|---|---|---|
| 3,986,553 | 10/1976 | Klyen | 166/264 X |
| 4,254,830 | 3/1981 | Garney et al. | 166/264 X |
| 4,438,654 | 3/1984 | Torstensson | 166/264 X |

Primary Examiner—Michael Powell Buiz
Attorney, Agent, or Firm—David G. Henry

[57] ABSTRACT

Applicant's invention is of an improved liquid sampling apparatus designed for collection of liquid, typically water, for sampling purposes. The improvement to existing bailer designs lies in re-contouring the proximal and distal surfaces to avoid the potentially costly effects of a presently available bailer's angular margins lodging against irregularities on the surface of well casings. The terminal ends of Applicant's bailer are generally dome-shaped, thereby eliminating angular margins which can engage surrounding protrusions or obstructions and intractably lodge the bailer in a well casing.

5 Claims, 1 Drawing Sheet

LIQUID SAMPLING APPARATUS

BACKGROUND OF THE INVENTION

1. Field of the Invention

Applicant's invention relates to apparatuses for retrieving liquid samples from reservoirs of liquid.

2. Background Information

Pollution of groundwater is a prevalent problem in today's environment. Pollutants from countless sources are fouling wells and underground aquifers at an alarming rate.

When investigating possible pollution of ground water, samples are taken both from producing water wells used to obtain potable water, as well as from test wells the sole purpose of which are to enable ground water sampling. The taking of test well samples are particularly prevalent within close proximity to such things as petroleum storage facilities, land fills, etc., ground water samples are taken and analyzed. In the case of most modern wells, the conduit ("well casing") which lines the hole ("well bore") which, in turn, defines the well is a mere pipe of rather small diameter. Wells of particularly modern vintage often have well casings of mere PVC pipe.

Presently, most water samples for testing purposes are taken through use of apparatuses known as "bailers." A bailer is an elongate, slender tube which is sized to pass through the narrow pipe which defines the well casing. The lower, insertion end of more advanced bailer designs includes a one-way valve which allows water to flow into the bailer as it is lowered into a body of water, but which hinders effluent flow as the bailer is lifted from the water.

So long as the well bore is in perfect condition (straight and unobstructed), a user of presently available bailers will not likely encounter serious difficulties. However, many (if not most) well casings are not in perfect condition after only a short life span. Shifting strata peripheral to the well casing and foreign obstructions within the casing render the well bore other than straight and smooth and can create serious problems for a user of presently available bailers, probably most notably when cracks appear in the well casing. Because the diameter of most well bores are little larger than the bailers themselves, cracks in the well casing, lateral diversions of the casing, and foreign obstructions which are lodged in the well casing can engage the angular margins and protrusions which are present on exterior surfaces of all presently available bailers. This can result in a catastrophic situation where the "stuck" bailer must be removed through very expensive well repair operations.

Many specific situations can result in a stuck bailer. One is when a substantially horizontal well casing crack occurs such that the casing on above the crack extends further into the casing lumen than the casing material below the crack. In this situation, the crack may at first be undetectable to the bailer user as the bailer is lowered into the well, The more recessed portion of the casing material below the crack will not "catch" a lower edge of the bailer. However, as the bailer is raised for removal from the well, the upper, angular margin of the bailer lodges against the protruding, overhanging, upper margin of the crack in the well casing. Unless the bailer user is able to coax the bailer past the crack, a very serious problem exists whereby the well will be unusable until the site of the obstruction is accessed through potentially very expensive drilling or digging operations. In the case of a water supply well, this usually represents an emergency situation requiring more expedited, and accordingly more expensive remedial measures.

This same fate awaits one who lowers a bailer past a foreign obstruction, only to find that the angular margin of the rising bailer engages the obstruction and moves it to a position which irreversibly prevents further upward movement. Typically in this situation, the obstruction acts as a latch which repeatedly moves to block upward movement of the bailer each time upward movement is attempted.

Even in situations where a stuck bailer is not so catastrophic an event, such as when one of many test wells in a small area is rendered inoperative, the problem still exists of not obtaining the test specimen which obviously was important enough to warrant a test in the first place. The well this case will still ultimately have to be repaired, or worse, unscrupulous practitioners may falsify results as if test specimens were successfully obtained from the subject well. In this latter event, potentially vital warning signs of pollution problems may go unnoticed.

An improved bailer design is needed to reduce the likelihood of intractably stuck bailers.

SUMMARY OF THE INVENTION

It is an object of the present invention to provide a novel bailer which facilitates easier passage of obstructions and protrusions in well casings.

It is another object of the present invention to provide a bailer which presents no angular margins to surrounding well casing when passing into or out of a well.

It is another object of the present invention to provide a bailer which, because of its lessened tendency to lodge against irregularities in well casings, reduces the likelihood that the bailer will become intractably lodged in a well casing.

In satisfaction of these and related objectives, Applicant's present invention provides a bailer of an improved design. Applicant's bailer exhibits dome-shaped termini which, together with the conduit portion therebetween, define an exterior surface contour devoid of angular margins or protrusions. The bailer of Applicant's design presents no margin or protrusion which can engage a surface aberration in a well casing so as to intractably lodge the bailer in the well casing.

DETAILED DESCRIPTION OF THE PREFERRED EMBODIMENT

Figure 1:
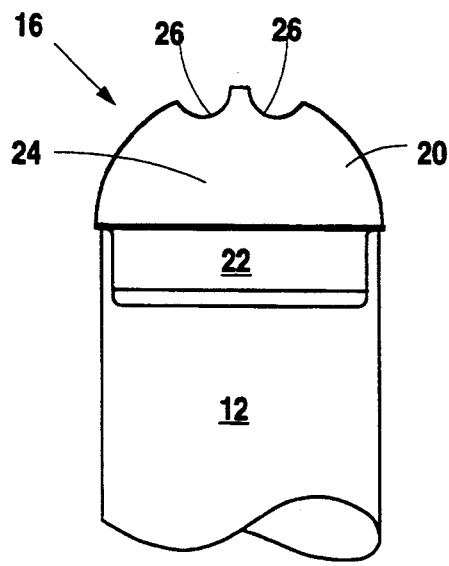
FIG. 1 is an elevational side view of the proximal end of Applicant's bailer.
Figure 3:
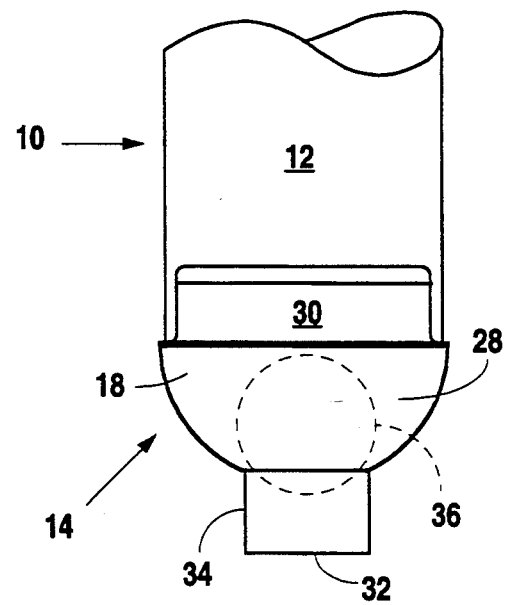
FIG. 3 is an elevational side view of the distal end of Applicant's bailer.
Figure 2:
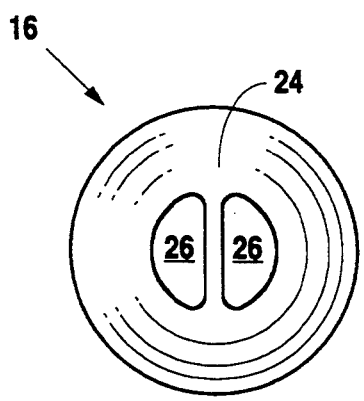
FIG. 2 is a top plan view of the proximal end of Applicant's bailer, looking at the convex side of the proximal terminus cap.
Figure 4:
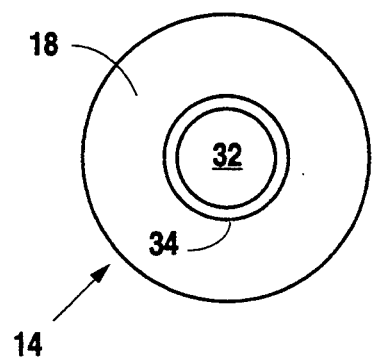
FIG. 4 is a bottom plan view of the distal end of Applicant's bailer, looking at the convex side of the distal terminus cap.

Referring to FIG. 1, the bailer of Applicant's invention is identified by the reference numeral 10. The preferred embodiment of bailer 10 includes a cylindrical, plastic tube 12.

The bailer has an insertion or distal end 14 and a proximal end 16. The preferred embodiment of Applicant's bailer 10 includes a distal terminus cap 18 and a proximal terminus cap 20. Proximal terminus cap 20 includes a generally dome-shaped portion 24 from which extends a nesting lip 22.

Nesting lip 22 extends from the margin of the dome portion 24 of cap 20 to generally define a cylindrical structure which snugly nests within the lumen of plastic tube 12. To insure that proximal terminus cap 20 does not accidentally disengage from plastic tube 12, the two should be suitably bonded together (such as through use of sonic welding) during assembly of bailer 10 through means appropriate for the material from which bailer 10 is fabricated (polyethylene in the case of Applicant's current preferred embodiment).

The preferred embodiment of proximal terminus cap 20 has two attachment orifices 26 passing through the dome-shaped portion 24. Attachment orifice 26 provide the means by which bailer 10 is attached to cording (not shown in the drawings) by which bailer 10 will be lowered into and removed from a well.

A terminal segment of cording will be passed through a first orifice 26 from the convex side of dome-shaped portion 24, and then passed through the other orifice 26 from the concave side of dome-shaped portion 24. In order to insure that bailer 10 assumes as near a vertical orientation as possible as it is suspended from a cord during sample taking, orifices 26 should reside as mirror images of each other on either side of a bisecting line which divides equally the dome-shaped portion 24 of terminus cap 20. For the same reason, the axis of symmetry of dome-shaped portion 24 should, when terminus cap 20 is installed on plastic tube 12, correspond to the longitudinal axis of symmetry of plastic tube 12.

The configuration of proximal terminus cap 20 as just described virtually eliminates the possibility of a bailer 10 becoming lodged against some irregularity in the well casing surface. Unlike the angular margins of presently available bailers, the purely rounded surfaces of Applicant's bailer 10 will simply slide past all obstructions in the well casing, except those which would have prevented initial insertion of bailer 10 in the first place.

Distal terminus cap 18 also includes a generally dome-shaped portion 28 from which extends a nesting lip 30. Nesting lip 30 is configured substantially identically to nesting lip 22 of proximal terminus cap 20 and is attached in the same manner.

The preferred embodiment of distal terminus cap 18 exhibits an intake orifice 32 through which water passes when gathering a test sample. The orifice 32 is, in the preferred embodiment surrounded by an annular flange 34 which serve to prevent interference with operation of the ball valve 36 by objects which may contact the distal end 14 of bailer 10.

As with proximal terminus cap 20, distal terminus cap 18 is configured whereby the axis of symmetry of dome-shaped portion 28 should, when terminus cap 18 is installed on plastic tube 12, correspond to the longitudinal axis of symmetry of plastic tube 12. The orifice 32 is, in turn, centered on the same axis of symmetry of plastic tube 12. This configuration insures that orifice 32 (and flange 34) is directed parallel with the path of bailer 10 and is less likely to scrap sediment, etc. from the casing wall as the bailer 10 is lowered for sample gathering, and thereby risk contamination of the sample.

While the greater concern which is addressed by the rounding of margins for bailer 10 is that of avoiding juxtaposition of a proximal, angular margin with a casing surface irregularity after the bailer is inserted into a well casing, the rounding of the distal end 14 surfaces of bailer 10 also has significant utility.

Certain irregularities in well casings are not so profound as to risk trapping the bailer 10 in the well casing. Nevertheless, some irregularities may be pronounced enough such that an angular margin on the distal end of a bailer will abut the irregularity and thereby suspend the bailer above the level intended for sample taking. Additionally, the engagement of a sharp edge with a well casing wall as the bailer is lowered may dislodge sediments and other accumulations on the well casing surface which may lead to local contamination of the underlying water supply to an extent which may render the sample unrepresentative of the actual over-all state of the water supply. In certain cases, this could lead to a "false positive" for serious levels of contaminants in a water supply, with potentially very costly and disquieting results. If, for example, a well test revealed an abnormal level of, perhaps, a heavy metal which had accumulated on the casing wall over time, but which was not at dangerous levels in the actual water supply, environmental regulations might, in the case of a producing water well, dictate suspension of operation of the subject well, and in other cases lead to costly investigations of nearby candidates for sources of pollution.

Therefore, the utility of both the rounding of proximal and distal surfaces for Applicant's bailer cannot be overestimated.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A liquid sampling apparatus comprising:
    an elongate, substantially cylindrical conduit member having first and second conduit ends;
    a first conduit member terminus, said first conduit member terminus being shaped to generally define a first convex dome extending outwardly from said conduit member at said first conduit end, said first convex dome portion of said first conduit member terminus being substantially centered on the longitudinal axis of symmetry of said conduit member, said convex dome portion having cord attachment means;
    a second conduit member terminus, said second conduit member terminus being shaped to generally define a second convex dome extending outwardly from said conduit member at said second conduit end, said second convex dome portion of said second conduit member terminus being substantially centered on the longitudinal axis of symmetry of said conduit member, said second conduit member terminus having an in-take orifice defined therethrough and a valve member for valving passage of fluid through said in-take orifice.

2. The apparatus of claim 1 wherein said cord attachment means consists of first and second attachment orifices defined through said dome portion of said first conduit member terminus and separated by a portion of said dome portion of said first conduit member terminus, whereby a terminal end of an elongate cording member may pass into said apparatus through said first attachment orifice and exit said apparatus through said second attachment orifice whereafter said terminal end of said cording member may be secured to a medial portion of said cording member to secure an attachment between said cording member and said apparatus.

3. The apparatus of claim 1 wherein said first terminus member is a removable cap-like member having a first nesting lip extending from the circumferential margin of said first convex dome, said first nesting lip being configured for reversibly, slidably and snugly nesting within said conduit member at said first conduit member end for reversibly attaching said first terminus member to said conduit member.

4. The apparatus of claim 1 wherein said second terminus member is a removable cap-like member having a second nesting lip extending from the circumferential margin of said second convex dome, said second nesting lip being configured for reversibly, slidably and snugly nesting within said conduit member at said second conduit member end for reversibly attaching said second terminus member to said conduit member.

5. The apparatus of claim 1 wherein said in-take orifice is defined by said second convex dome whereby said in-take orifice is centered on an axis of symmetry of said second convex dome.

* * * * *